(12) United States Patent
Weiss

(10) Patent No.: US 11,450,163 B1
(45) Date of Patent: Sep. 20, 2022

(54) SYSTEM AND METHOD FOR THE SECURE DELIVERY AND SANITIZATION OF PACKAGES

(71) Applicant: Templar Contracting, Inc., Trinity, FL (US)

(72) Inventor: Regan S. Weiss, New Port Richey, FL (US)

(73) Assignee: Forty Three Marketing and Consulting Inc., New Port Richey, FL (US)

( * ) Notice: Subject to any disclaimer, the term of this patent is extended or adjusted under 35 U.S.C. 154(b) by 0 days.

(21) Appl. No.: 16/905,996

(22) Filed: Jun. 19, 2020

Related U.S. Application Data

(60) Provisional application No. 62/864,597, filed on Jun. 21, 2019.

(51) Int. Cl.
| | |
|---|---|
| G07C 9/00 | (2020.01) |
| A61L 2/10 | (2006.01) |
| G05B 15/02 | (2006.01) |
| G06Q 10/08 | (2012.01) |
| G07C 9/30 | (2020.01) |
| A61L 2/26 | (2006.01) |
| H04N 7/18 | (2006.01) |

(52) U.S. Cl.
CPC ............ *G07C 9/00912* (2013.01); *A61L 2/10* (2013.01); *A61L 2/26* (2013.01); *G05B 15/02* (2013.01); *G06Q 10/0832* (2013.01); *G07C 9/30* (2020.01); *A61L 2202/11* (2013.01); *A61L 2202/23* (2013.01); *H04N 7/183* (2013.01)

(58) Field of Classification Search
CPC ......... G07C 9/00912; G07C 9/30; A61L 2/10; A61L 2/26; A61L 2202/11; A61L 2202/23; G05B 15/02; G06Q 10/0832; H04N 7/183
See application file for complete search history.

(56) References Cited

U.S. PATENT DOCUMENTS

| | | | | |
|---|---|---|---|---|
| 5,388,391 | A * | 2/1995 | Parker | B30B 9/3017 53/238 |
| 6,415,552 | B1 * | 7/2002 | Khosropour | F25D 23/12 52/27 |
| 6,923,367 | B1 * | 8/2005 | Grossman | A47G 29/1216 232/29 |
| 10,255,737 | B1 * | 4/2019 | Eichenblatt | G06Q 20/18 |
| 2003/0168507 | A1 * | 9/2003 | Mihaylov | A61L 2/10 232/45 |
| 2004/0140347 | A1 * | 7/2004 | Mihaylov | A47G 29/1212 232/31 |

(Continued)

*Primary Examiner* — Thomas D Alunkal
(74) *Attorney, Agent, or Firm* — GrayRobinson, P.A.; Michael J. Colitz, III

(57) ABSTRACT

Disclosed is a delivery portal for a residential home. The portal can be accessed by delivery personnel via an exterior door. A lock on the exterior door is controlled via a key code or similar authentication means. Once accessed, the delivery personnel can leave packages in a climate controlled environment. A refrigerator can be provided within the portal for food items. Ultraviolet lighting can be provided for sanitizing packages. Residents access the portal through a separate, interior door. Preferably, the locks on the interior and exterior doors are computer controlled to prevent both being unlocked at the same time. This avoids residents coming into contact with delivery personnel.

8 Claims, 4 Drawing Sheets

(56) References Cited

U.S. PATENT DOCUMENTS

| | | | |
|---|---|---|---|
| 2004/0211527 A1* | 10/2004 | Humble | E04F 10/0614 160/59 |
| 2019/0231106 A1* | 8/2019 | Kaiserman | F25D 23/10 |
| 2020/0360549 A1* | 11/2020 | Neveu | A61B 50/33 |

* cited by examiner

SYSTEM AND METHOD FOR THE SECURE DELIVERY AND SANITIZATION OF PACKAGES

CROSS REFERENCE TO RELATED APPLICATIONS

This application claims priority to and is a continuation of Provisional Application Ser. No. 62/864,597 filed on Jun. 21, 2019 and entitled "Secure Delivery Portal for Residential Homes." The contents of this application are incorporated herein for all purposes.

TECHNICAL FIELD

This disclosure relates to a delivery portal. More particularly, the present disclosure relates to a portal that is connected to a residential home and that is configured to both secure and sanitize packages.

BACKGROUND OF THE INVENTION

E-commerce is an ever growing share of the U.S. economy. More than ever before, consumers are enjoying the benefits of shopping from home and having packages delivered to their doorstep. Companies like Amazon®, Ebay®, and Walmart® are continually reducing delivery times, increasing inventories, and offering free shipping, all of which are making on-line shopping all the more attractive. But this convenience comes with a downside as ordered items often arrive when consumers are working or are otherwise not at home. The result is that valuable packages are often left on the consumer's door step. This invites theft from "porch pirates" who roam neighborhoods looking for unsecured packages. Yet another downside is that deliveries that are left on the doorstep can get damaged as a result of excessive heat, cold, wind, and rain.

Home food deliveries are also on the rise. Companies like Doordash®, Uber Eats®, and Grubhub® offer an expedient way for consumers to order the meal of their choice from local restaurants and eateries. Still yet other services allow for the convenient delivery of groceries. But these food and grocery delivery services also suffer from the fact that deliveries may arrive at inconvenient times. This can result in spoiled or rotten food. And regardless of what is being delivered, some consumers are simply reluctant to open their doors to unknown delivery personnel.

There is also an increased need for sanitizing and disinfecting packages that are brought into the home. This is most recently the result of an on-going worldwide pandemic. However, it is believed that even when the current pandemic subsides, consumers will continue to be vigilant and demand that any new items brought into a home be sanitized.

What is needed, therefore, is a secure portal that is accessible by delivery personnel and that can safely store packages and food items until the consumer is ready to retrieve them. There is also a need in the art for a delivery system that sanitizes packages once in the residence. The secure delivery portal of the present disclosure is designed to fulfill these and other shortcomings present with known delivery systems.

SUMMARY OF THE INVENTION

This disclosure relates to a secure delivery portal for a residential home.

The disclosed portal has several important advantages. For example, the portal allows delivered items to be secured until retrieved by the consumer.

Another advantage is realized by providing a delivery portal that includes a refrigerated space that allows perishable items to be stored until retrieved.

A further possible advantage is achieved by employing a camera or sensor that allows consumers to remotely monitor the delivery process.

Still yet another possible advantage is achieved by providing an exterior door that can only be unlocked with a unique passcode that is provided to the delivery personnel.

Another advantage is attained by providing an exterior door that can only be unlocked if an associated interior door is locked, thereby precluding delivery personnel from gaining access to the residence.

Still yet another advantage is attained by using ultraviolet lighting to destroy germs and bacteria on packages within the delivery portal.

Various embodiments of the invention may have none, some, or all of these advantages. Other technical advantages of the present invention will be readily apparent to one skilled in the art.

BRIEF DESCRIPTION OF THE DRAWINGS

For a more complete understanding of the present disclosure and its advantages, reference is now made to the following descriptions, taken in conjunction with the accompanying drawings, in which.

Similar reference numerals refer to similar parts throughout the several views of the drawings.

| Parts List | |
|---|---|
| 20 Residence | 36 Home Office |
| 22 Portal | 38 Double Doors |
| 24 Main Entrance | 40 Packages |
| 26 Exterior Door | 42 Shelving |
| 28 Interior Door | 44 Refrigerator |
| 32 Porch | 46 Camera |
| 34 Bedroom | 48 Locks |
| | 52 Keypad |

DETAILED DESCRIPTION OF THE DRAWINGS

The present disclosure relates to a delivery portal for a residential home. The portal can be accessed by delivery personnel via an exterior door. A lock on the exterior door is controlled via a key code or similar authentication means. Once accessed, the delivery personnel can leave packages in a climate controlled environment. A refrigerator can be provided within the portal for storing food items. Residents can access the portal through a separate, interior door. Preferably, the locks on the interior and exterior doors are computer controlled to prevent both being unlocked at the same time. This avoids residents coming into contact with delivery personnel. The various features of the present system, and the manner in which they interrelate, are described in greater detail hereinafter.

Figure 1:
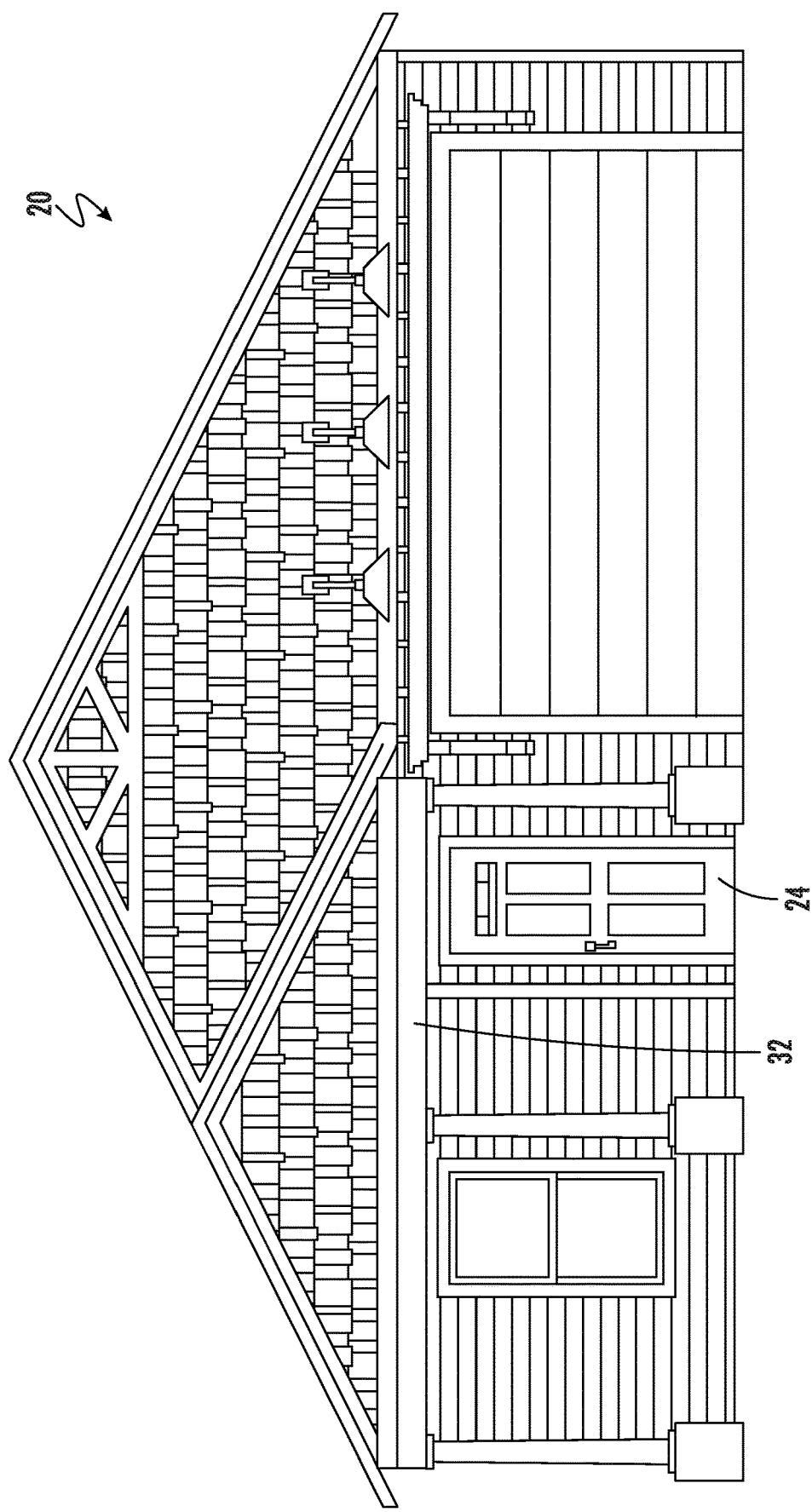
FIG. 1 is an elevational view of a home with a secure delivery portal.
Figure 2:
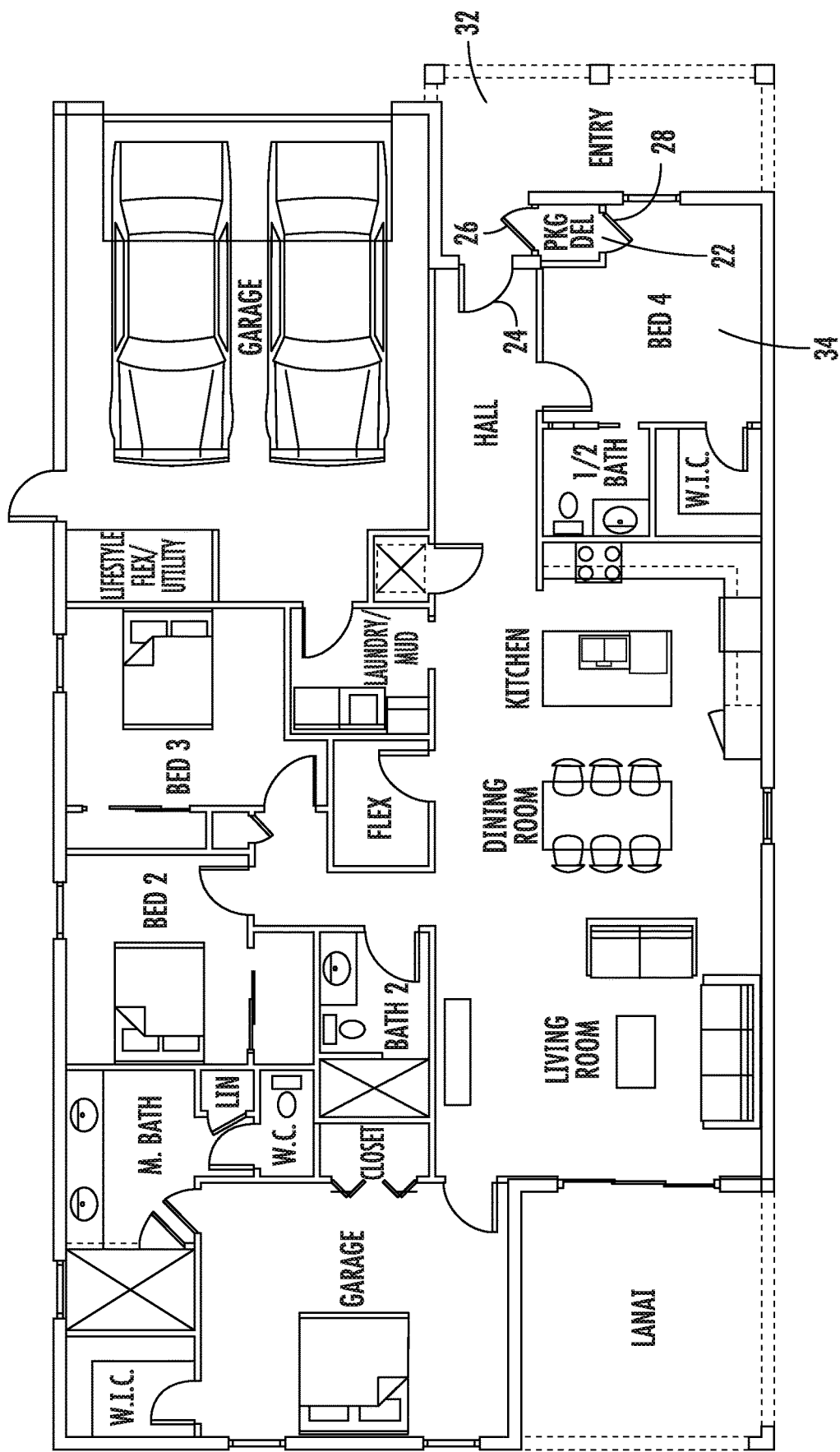
FIG. 2 is a floor plan for a home with a secure delivery portal.

Embodiments of FIGS. 1 and 2

FIG. 1 illustrates a residence 20 employing the delivery portal 22 of the present disclosure. As is typical, residence 20 includes a door (or doors) that constitutes the main entryway 24 for the home. As illustrated in FIG. 2, delivery portal 22 of the present invention includes an exterior door 26, which would typically be positioned adjacent the main entryway 24, and an interior door 28. Both the main entryway 24 and exterior door 26 can be positioned under a porch 32 or awning. As further illustrated in FIG. 2, portal 22 leads into a bedroom 34 and is accessible from a covered porch 32. It includes exterior and interior doors (26 and 28). Exterior door 26 of portal 22 is positioned adjacent to main entrance 24 to residence 20.

Figure 3:
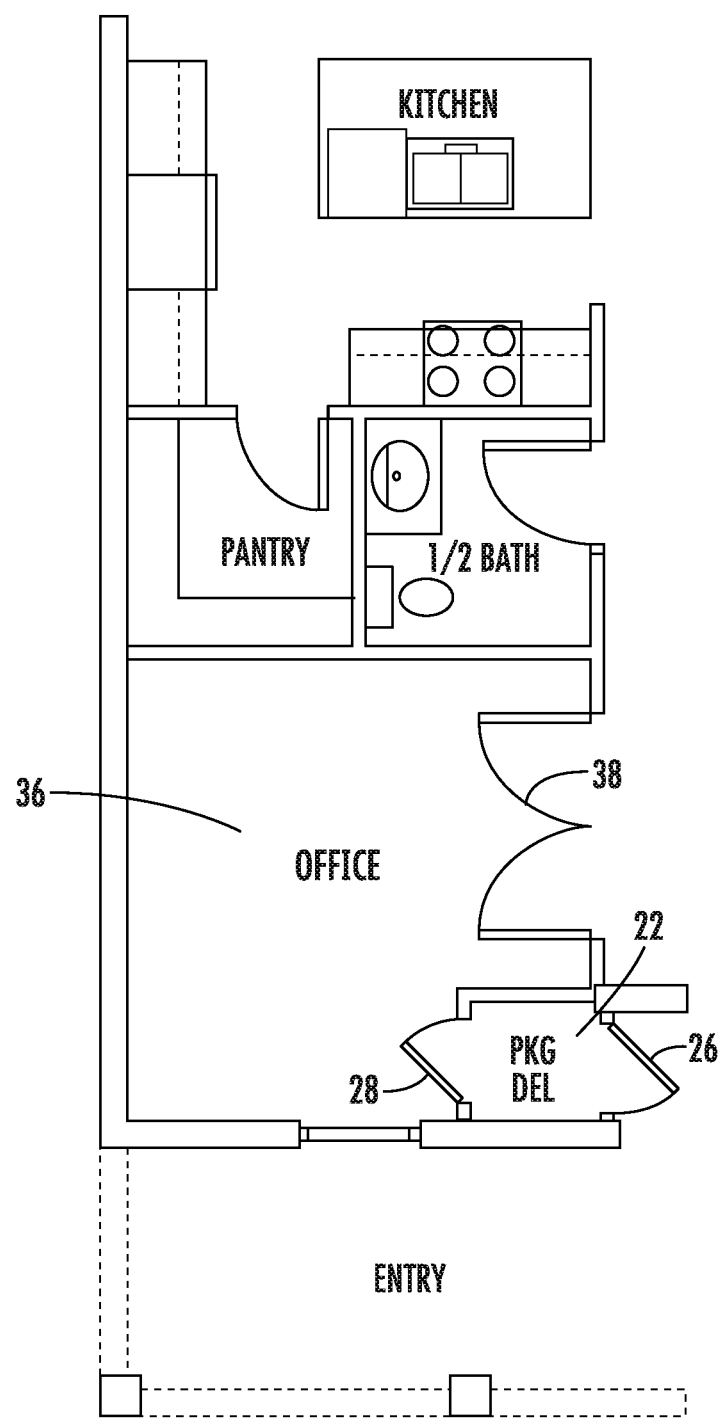
FIG. 3 is a detailed floor plan of the secure delivery portal.
Figure 4:
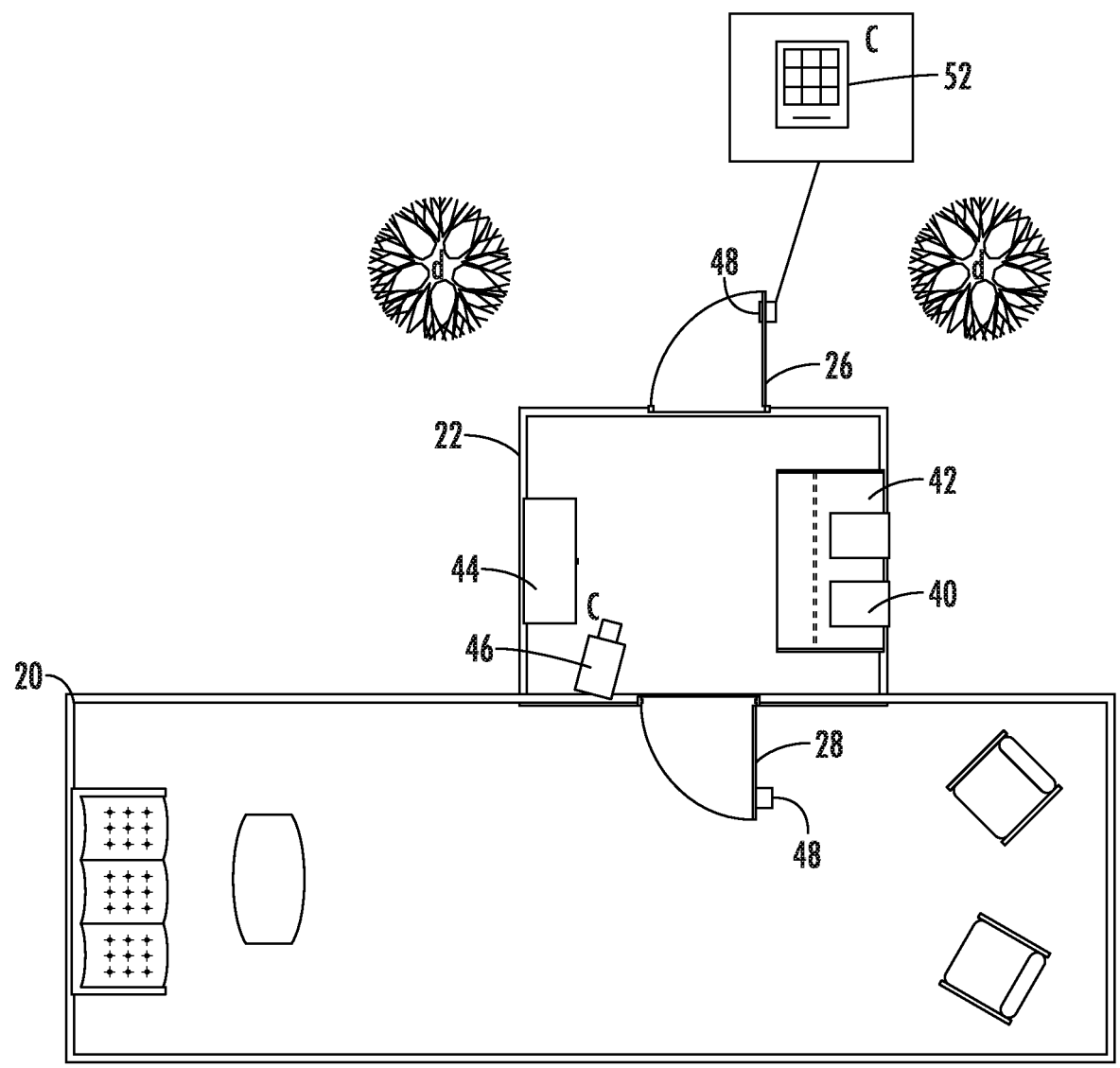
FIG. 4 is an additional floor plan of the secure delivery portal.

Embodiments of FIGS. 3 and 4

FIG. 3 illustrates a delivery portal 22 leading into a home office 36 and adjacent to a set of two doors 38 leading into the same office. FIG. 4 illustrates yet another embodiment of delivery portal 22 of the present disclosure. Delivery portal 22 may include shelving 42 for storing packages 40 or other delivered items. A refrigerator 44 can also be included within portal 22 to allow perishable items to be stored. The interior of portal 22 will also be climate controlled, preferably by the HVAC system employed by the main residence 20. Nonetheless, it is within the scope of the present invention for portal 22 to have a separately controlled HVAC system. In one embodiment, portal 22 includes ultraviolet lighting to reduce bacteria or germs. The doors (26 and 28) are preferably impact rated and include necessary weather stripping to appropriately weather proof the interior of portal 22.

Additional Embodiments

In one aspect of the invention, the interior of portal 22 includes a security camera 46 to allow residents to monitor the activities of delivery personnel and to verify the delivery of packages 40. Sensors can also be mounted upon the shelving 42 or within the refrigerator unit 44 to confirm the placement of delivered items.

In yet another aspect of the invention, both the exterior and interior doors to the portal 22 include computer controlled locks 48. The locks 48 can be, for example, dead bolts that are controlled by a solenoid or similar mechanism. The computer control regulates the locking and unlocking of the exterior and interior door locks 48. In one embodiment, the control precludes both doors being unlocked at the same time. This ensures that the interior door 28 cannot be opened when a delivery is in progress. This, in turn, prevents residents from coming into contact with delivery personnel. It further prevents delivery personnel from gaining access to the residence. The lock 48 of the exterior door 26 can further by controlled by a keypad 52. This allows a unique access code to be provided to the delivery personnel by the resident. This keeps the interior of the portal 22 secure and prevents the theft of delivered packages 40.

System and Method

The system described above allows packages to be securely delivered by delivery personnel into a residence while eliminating interactions between the delivery personnel and the residents. It further allows those packages to be sanitized. This is achieved by providing a room within the residence that includes an interior door accessible by the residents. The interior door can be selectively placed in either a secured or an unsecured state (i.e. locked or unlocked) by a resident via a computer controlled deadbolt.

The package portal is adapted to receive packages from the delivery personnel and is interconnected to the room via the interior door. The package portal also includes an exterior door that can be accessed by the delivery personnel from outside of the residence. The exterior door can be selectively placed in either a secured or an unsecured state (i.e. locked or unlocked) by the delivery personnel. This can be accomplished via a keypad on the exterior door. The computer control precludes the interior and exterior doors from being simultaneously unlocked, thereby eliminating interactions between the delivery personnel and the residents.

A refrigerator is positioned within the package portal for the purpose of storing packages containing perishable items. Residents can monitor the delivery of packages by the delivery personnel via a camera within the delivery portal. Finally, ultraviolet lighting is positioned within the package portal and can be turned on following the delivery of packages by the delivery personnel for the purpose of killing germs and bacteria present on any packages.

The method of the present invention is next described. In the first step, delivery personnel are granted access to the delivery portal by simultaneously unlocking the exterior door and locking the interior door. Thereafter, the delivery personnel delivers one or more packages to the individual by leaving it within the delivery portal. Next, upon the departure of the delivery personnel, a resident accesses the room by simultaneously locking the exterior door and unlocking the interior door. Finally, the individual retrieves the package left by the delivery personnel.

Although this disclosure has been described in terms of certain embodiments and generally associated methods, alterations, and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure.

What is claimed is:

1. A system for allowing packages to be securely delivered by delivery personnel into a residence while eliminating interactions between the delivery personnel and the residents, the system comprising:
   a room within the residence, the room including an interior door to be accessed by the residents, the interior door being selectively placed in either a secured or an unsecured state by a resident via a computer controlled deadbolt;
   a package portal for receiving packages from the delivery personnel, the package portal being interconnected to the room via the interior door, the package portal including an exterior door to be accessed by the delivery personnel and for providing access to the package portal from outside of the residence, the exterior door being selectively placed in either a secured or an unsecured state by the delivery personnel, the computer control precluding the interior and exterior doors from being simultaneously placed in an unsecured state, thereby eliminating interactions between the delivery personnel and the residents;

a refrigerator positioned within the package portal, the delivery personnel having access to the refrigerator for the purpose of storing packages containing perishable items;

a camera positioned within the package portal for allowing residents to monitor the delivery of packages by the delivery personnel;

ultraviolet lighting positioned within the package portal and being turned on following the delivery of packages by the delivery personnel, the ultraviolet lighting being used to kill germs and bacteria present on any packages.

2. A system for allowing packages to be securely delivered by delivery personnel into a residence comprising:

a room within the residence, the room including an interior door to be accessed by the residents, the interior door being selectively placed in either a secured or an unsecured state by a resident via a computer controlled deadbolt;

a package portal for receiving packages from the delivery personnel, the package portal being interconnected to the room via the interior door, the package portal including an exterior door to be accessed by the delivery personnel and for providing access to the package portal from outside of the residence, the exterior door being selectively placed in either a secured or an unsecured state by the delivery personnel, the computer control precluding the interior and exterior doors from being simultaneously placed in an unsecured state, thereby eliminating interactions between the delivery personnel and the residents ultraviolet lighting positioned within the package portal and being turned on following the delivery of packages by the delivery personnel, the ultraviolet lighting being used to kill germs and bacteria present on any packages.

3. The system as described in claim 2 further comprising a refrigerator positioned within the package portal, the delivery personnel having access to the refrigerator for the purpose of storing packages containing perishable items.

4. The system as described in claim 2 further comprising a camera positioned within the package portal for allowing residents to monitor the delivery of packages by the delivery personnel.

5. The system as described in claim 2 wherein the residence further comprises a main entry door and an awning and wherein both the main entry door and the exterior door are underneath the awning.

6. A method for allowing delivery personnel to securely deliver sanitized packages to an individual within a residence, the method comprising the following steps:

providing a delivery portal and a room as part of the residence, the delivery portal and the room being interconnected via an interior door, an exterior door providing access to the delivery portal from outside the residence, the interior and exterior doors being selectively locked or unlocked by the individual via computer controlled deadbolts;

granting the delivery personnel access to the deliver portal by simultaneously unlocking the exterior door and locking the interior door, the delivery personnel delivering a package to the individual by leaving it in the delivery portal;

ultraviolet lighting being turned on following the delivery of packages by the delivery personnel, the ultraviolet lighting being used to kill germs and bacteria present on any packages;

granting the individual access to the room by simultaneously locking the exterior door and unlocking the interior door, the individual retrieving the package left by the delivery personnel.

7. The method as described in claim 6 comprising the additional steps of providing a camera within the delivery portal and monitoring the delivery of the package via the camera.

8. The method as described in claim 6 comprising the additional step of providing a refrigerator within the delivery portal and giving the delivery personnel access to the refrigerator for the purpose of storing packages containing perishable items.

* * * * *